United States Patent
Takai et al.

(10) Patent No.: US 6,743,925 B1
(45) Date of Patent: Jun. 1, 2004

(54) NITROIMIDAZOLE DERIVATIVE AND DIAGNOSTIC IMAGING AGENT CONTAINING THE SAME

(75) Inventors: Yoshihiro Takai, 2-14, Nijino-oka 3-chome, Izumi-ku, Sendai-shi, Miyagi (JP), 981-8007; Tatsuo Ido, 9-14, Miyagidai 3-chome, Aoba-ku, Sendai-shi, Miyagi (JP), 989-3214; Michihiko Tsujitani, Kanagawa (JP)

(73) Assignees: Pola Chemical Industries, Inc., Shizuoka (JP); Yoshihiro Takai, Sendai (JP); Tatsuo Ido, Sendai (JP)

( * ) Notice: Subject to any disclaimer, the term of this patent is extended or adjusted under 35 U.S.C. 154(b) by 0 days.

(21) Appl. No.: 10/070,899
(22) PCT Filed: Sep. 12, 2000
(86) PCT No.: PCT/JP00/06226
§ 371 (c)(1),
(2), (4) Date: Aug. 7, 2002
(87) PCT Pub. No.: WO01/19799
PCT Pub. Date: Mar. 22, 2001

(30) Foreign Application Priority Data

Sep. 13, 1999 (JP) ............................................. 11/259057
Sep. 14, 1999 (JP) ............................................. 11/260315

(51) Int. Cl.$^7$ ............................................. C07D 233/91
(52) U.S. Cl. ....................... 548/327.5; 424/9.1; 424/9.3; 424/9.4; 424/9.5; 424/9.6; 424/9.7; 424/9.8
(58) Field of Search ........................ 548/327.5; 424/9.1, 424/9.3, 9.4, 9.5, 9.6, 9.7, 9.8

(56) References Cited

U.S. PATENT DOCUMENTS 5,728,843 A 3/1998 Wallace et al.
5,843,404 A 12/1998 Koch et al.

FOREIGN PATENT DOCUMENTS

EP 0 312 858 4/1989

OTHER PUBLICATIONS

Hiroaki Wada et al.: "Synthesis of 1–'2–'18Flfluoro–1–(hydroxymethyl)–ethoxy? potential agent for imaging hypoxic tissues by PET" J. Labelled Compd. Radiopharm., 43(8), pp. 785–793 07/00.

M.M Alauddin et al.: "Evaluation of 9–'(3–F–fluoro–1–hydroxy–2–propoxy)methyll guanine ('FI–FHPG) in vitro and in vivo as a probe for PET imaging of gene incorporation and expression in tumors—Initial evaluation with PET with the radiolabeled glucose analogue" Nuclear Medicine and Biology, vol. 26, No. 4, pp. 371–376 05/99.

J.E. Biskupik et al.: "Synthesis of an (iodovinyl)misonidazole Derivative for hypoxia imaging" Journal of Medicinal Chemistry, vol. 34, pp. 2165–2168, 1991.

T.J. Tewson: "Synthesis of 'F!Fluoroetanidazole: A potential new tracer for imagine hypoxia" Nuclear Medicine and Boiolgy, vol. 24, No. 8, pp. 755–760 Nov. 1, 1997.

M.M. Alauddin et al.: "Synthesis and preliminary evaluation of 9–(4'F!–Fluoro–3–hydroxy methylbutyl)guanine ('F! FHBG): a new potential imaging agent for viral infection and gene therapy using PET–synthesis of 9–'(1–F–fluoro–3–hydroxy–2–propoxy)–methyl !guanine" Nuclear Medicine and Biology, vol. 25, No. 3, pp. 175–180 Apr. 1, 1998.

*Primary Examiner*—Laura L. Stockton
(74) *Attorney, Agent, or Firm*—Oblon, Spivak, McClelland, Maier & Neustadt, P.C.

(57) ABSTRACT

A nitroimidazole derivative represented by the following formula (1):

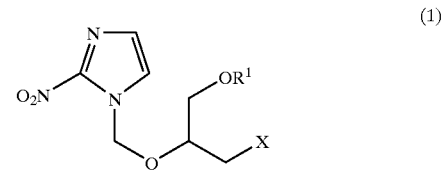

(1)

[wherein $R^1$ represents a hydrogen atom or a C1–C4 alkanoyl group; and X represents a fluorine atom or an isotope thereof], and a diagnostic imaging agent containing the derivative as an active ingredient.

The derivative enables imaging of the ischemic sites of a circulatory organ or imaging of cancer cells, and thus the derivative can provide information about the position and the amount of the ischemic sites or the cancer cells. Therefore, the derivative contributes to selection of appropriate treatment of ischemia or cancer.

17 Claims, 1 Drawing Sheet

NITROIMIDAZOLE DERIVATIVE AND DIAGNOSTIC IMAGING AGENT CONTAINING THE SAME

TECHNICAL FIELD

The present invention relates to a novel nitroimidazole. derivative which is useful as a diagnostic imaging agent.

BACKGROUND ART

In recent years, everyday foods in Japan have been Europeanized or Americanized, and in accordance with this trend, patients suffering diseases of the circulatory system, such as hyperlipidemia, angina pectoris, and myocardial infarction, have been drastically increasing. Such a disease may cause damage to nutrition-supplying organs of the body, such as the heart and blood vessels, and may be life threatening, depending on the progress of the disease. Therefore, the site of the disease must be determined at early stages of the disease and the disease must be subjected to appropriate treatment.

In ischemic diseases, peripheral tissues of ischemic sites are destroyed by active oxygen, and thus it is important not only to find the presence of vasoconstriction sites or heart valve disorder, but also to determine ischemic sites which are generated due to lack of blood flow. Briefly, damaged tissues at such ischemic sites, as well as vasoconstriction sites and cardiac dysfunction, may be life threatening.

In recent years, diseases of circulatory organs have been reliably diagnosed, and the sites of the diseases have been precisely determined through angiography, electrocardiogram, load electrocardiogram, or 24-hour monitoring. However, even when such a method is employed, ischemic sites or tissues cannot be detected directly, and biopsy has been the main means for detecting damage derived from ischemia. Therefore, there has been demand for means to determine ischemic sites conveniently and reliably.

Meanwhile, in treatment of cancer, it is important to detect the presence of cancer cells at early stages of tumor formation, in order to enhance the effect of chemotherapy or radiotherapy or to arrest the progress of cancer, such as by preventing metastasis. In recent years, it has been reported that, among cancer cells, there are hypoxic cells which are resistant to a chemotherapeutic agent or radiation. Therefore, the amount of such hypoxic cells and the position at which the cells exist must be detected, and then the cells must be eliminated.

Conventionally, a method in which a monoclonal antibody against a tumor marker is employed is known as a typical method for detecting and identifying cancer cells. However, in the method, although the presence or the amount of a tumor maker is determined, the position at which the marker is present cannot be detected.

In order to detect the position at which a tumor is present, there has been carried out an imaging method, such as magnetic resonance imaging (MRI) in which the distribution of water is determined through proton NMR, or X-ray imaging by use of an organic iodine compound. However, such a method is carried out for merely detecting difference in biophysical properties of the tumor, which is attributed to the cancer tissue, and the method does not image cancer cells directly. Therefore, such a method does not provide information about the presence of chemotherapeutic-agent-resistant or radiation-resistant cells, the information being an index of difficulty in treatment of the tumor.

In order to solve the aforementioned problems, an object of the present invention is to provide a compound which is useful for imaging cancer cells or ischemic sites of circulatory organs.

DISCLOSURE OF THE INVENTION

In view of the foregoing, the present inventors have performed extensive studies, and have found that a nitroimidazole derivative represented by the following formula (1) is selectively directed to ischemic sites of circulatory organs, or chemotherapeutic-agent-resistant or radiation-resistant hypoxic cancer cells; and that when the derivative is employed as a contrast medium in diagnostic imaging, the cells can be imaged. The present invention has been accomplished on the basis of these findings.

Accordingly, the present invention provides a nitroimidazole derivative represented by the following formula (1):

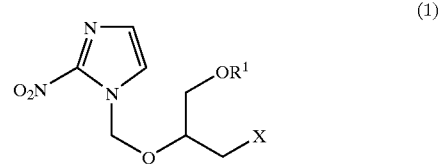

(1)

[wherein $R^1$ represents a hydrogen atom or a $C_1$–$C_4$ alkanoyl group, and X represents a fluorine atom or an isotope thereof].

The present invention also provides a diagnostic imaging agent comprising the nitroimidazole derivative (1) as an active ingredient.

The present invention also provides a nitroimidazole derivative represented by the following formula (2):

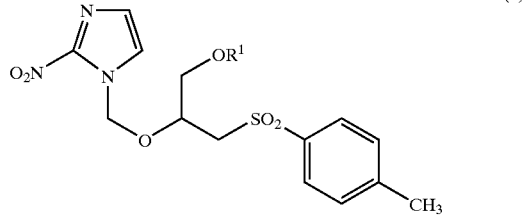

(2)

[wherein $R^1$ represents a hydrogen atom or a $C_1$–$C_4$ alkanoyl group], and a method for producing the nitroimidazole derivative represented by formula (1), comprising fluorination of the nitroimidazole derivative of formula (2).

BEST MODE FOR CARRYING OUT THE INVENTION

Figure 1:
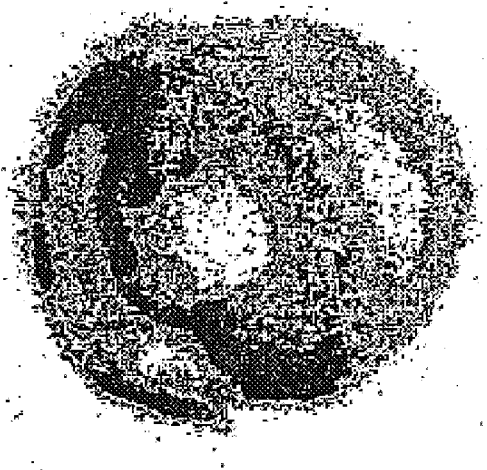
FIG. 1 is an autoradiogram of an ischemic heart, which is obtained by use of the diagnostic imaging agent of the present invention.

A nitroimidazole derivative represented by formula (1) of the present invention is a novel compound, and a fluorine atom or an isotope thereof represented by X in the formula is a stable isotope of fluorine ($^{19}F$) or a radioisotope of fluorine ($^{18}F$). When X is the radioisotope ($^{18}F$), the position of the derivative of the present invention in the body can be visualized through positron emission tomography (PET). When X is the non-radioactive stable isotope ($^{19}$F), the position of the derivative in the body can be visualized through MRI or a similar means. The derivative which does not comprise the radioisotope of fluorine plays an important role in imaging as an agent diluting the derivative comprising the radioisotope.

A $C_1$–$C_4$ alkanoyl group represented by $R^1$ may be an acetyl group, a propionyl group, a butyryl group, or an isobutyryl group, and is preferably an acetyl group.

In the present invention, $R^1$ is more preferably a hydrogen atom, in consideration of control of imaging.

In the present invention, examples of preferable nitroimidazole derivatives (1) include 1-[2-fluoro($^{18}$F or $^{19}$F)-1-(hydroxymethyl)ethoxy]methyl-2-nitroimidazole and 1-[1-acetoxymethyl-2-fluoro($^{18}$F or $^{19}$F)ethoxy]methyl-2-nitroimidazole.

The compound of the present invention (1) contains an asymmetric carbon atom, and thus there exist stereoisomers of the compound which are derived from the position of the carbon atom. The present invention encompasses the stereoisomers, and the streoisomers may be employed singly or in combination.

The nitroimidazole derivative (1) of the present invention may be produced through, for example, the following steps:

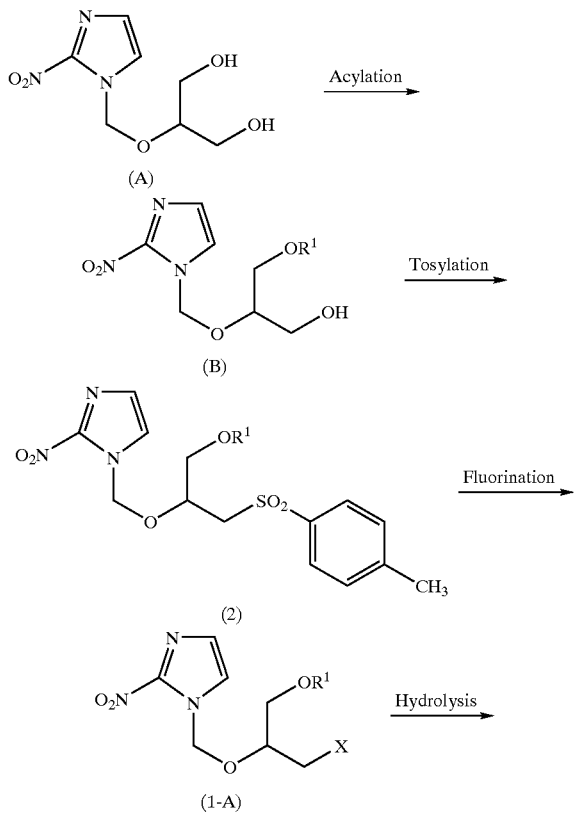

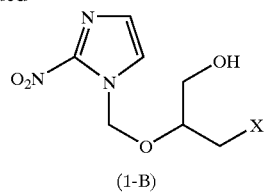

(1-B)

[wherein $R^1$ and X are identical to the aforementioned RX and X].

Firstly., a hydroxy form (A) is acylated to produce an ester form (B), and then the ester form is tosylated to produce a tosyl form (2) serving as a novel intermediate Subsequently, the tosyl form is fluorinated, producing a nitroimidazole derivative (1-A) of the present invention in which $R^1$ is an alkanoyl group. If desired, the derivative (1-A) may be subjected to hydrolysis, to thereby obtain a nitroimidazole derivative (1-B) of the present invention, in which $R^1$ is hydrogen.

Acylation may be carried out through a customary method; for example, may be carried out by use of an acid halide in a solvent at –30 to 100° C. for one to five hours in the presence or absence of an inorganic base, an organic base, or an organometallic compound. In acylation, an inorganic base may be potassium hydroxide, sodium carbonate, or cesium carbonate; an organic base may be pyridine, 4-dimethylaminopyridine, picoline, N,N-dimethylaniline, N-methylmorpholine, dimethylamine, triethylamine, or 1,8-diazabicyclo[5.4.0]undecene (DBU); and an organometallic compound may be dibutyl tin oxide. Examples of solvents which may be employed include halogenated hydrocarbons such as methylene chloride, chloroform, carbon tetrachloride, and chlorobenzene; aromatic hydrocarbons such as benzene and toluene; ethers such as tetrahydrofuran, diethyl ether, and dioxane; ketones such as acetone and methyl ethyl ketone; non-protonic polar solvents such as acetonitrile and N,N-dimethylformamide; and ethyl acetate.

Tosylation may be carried out through a customary method; for example, may be carried out by use of 2–3 mol of tosyl halide (e.g., tosyl chloride) with respect to 1 mol of a material compound in the presence of a base such as triethylamine in an organic solvent such as methylene chloride, acetonitrile, dimethylformamide, or pyridine at 0–100° C. for one to five hours.

Fluorination may be carried out in an inert solvent by use of crown ether serving as a catalyst and by use of a fluorination agent such as an alkali metal fluoride (e.g., sodium fluoride, potassium fluoride, or cesium fluoride) or a tetraammonium fluoride (e.g., tetrabutylammonium fluoride). An inert solvent is preferably a halogen solvent, an ether solvent, a hydrocarbon solvent, a polar solvent, or a solvent mixture thereof. Fluorination is usually carried out at about 70–130° C., and preferably at 100–120° C. in the case in which DMF is employed as a solvent.

When a fluoride of $^{18}$F (e.g., K$^{18}$F) is employed as a fluorination agent, fluorination is preferably carried out by use of cryptofix 2.2.2 serving as a phase transfer catalyst. A source of fluoride of $^{18}$F can be obtained by trapping an aqueous solution of $^{18}$F with an anion exchange resin and eluting the solution with an aqueous solution of potassium carbonate, the $^{18}$F solution being obtained from enriched H$_2$$^{18}$O by means of $^{18}$O (p, n).

Hydrolysis may be carried out in the presence of an inorganic base in a solvent at 0–100° C. for one to five minutes. An inorganic base may be potassium hydroxide, sodium hydroxide, potassium carbonate, sodium carbonate, or cesium carbonate. A solvent may be water; an alcohol such as methanol, ethanol, or propanol; an ether such as tetrahydrofuran, diethyl ether, or dioxane; or a ketone such as acetone or methyl ethyl ketone.

When the thus-produced nitroimidazole derivative (1) of the present invention is administered to a living organism, as shown in the below-described Test Examples, the derivative recognizes ischemic sites or a cancer cells and is rapidly directed thereto. Therefore, the derivative is useful as a diagnostic imaging agent, and when it is employed together with an apparatus for diagnostic imaging such as MRI, the position at which ischemic sites or cancer cells exist can be detected and the amount of the sites or cells can be measured.

The nitroimidazole derivative (1) of the present invention may be mixed with a pharmaceutically acceptable additive, to thereby produce a diagnostic imaging agent. Examples of such additives include pharmaceutically acceptable isotonic agents, emulsifying and dispersing agents, excipients, binders, coating agents, stabilizers, sugars such as mannitol, and freeze-dry-aiding agents such as amino acids.

The diagnostic imaging agent of the present invention may be administered orally or parenterally; for example, through a generally employed means such as intravenous injection. Particularly, the nitroimidazole derivative (1) comprising a hydrogen atom as R$^1$ is water-soluble and tends to be directed to and accumulated in ischemic smooth muscle cells, or chemotherapeutic-agent-resistant or radiation-resistant cells in a tumor, and thus the derivative may be administered in the dosage form of injection. Meanwhile, the nitroimidazole derivative (1) comprising an alkanoyl group as R$^1$ may be administered orally as a prodrug in the dosage form of enteric-coated drug, since the alkanoyl group easily undergoes dealkanoylation in a living organism.

The derivative of the present invention is preferably administered about 2–3 hours before radiography or MRI.

The dose of the diagnostic imaging agent of the present invention is determined in consideration of various conditions such as the weight, age, and sex of a patient, and an imaging apparatus which is employed. When the diagnostic imaging agent is employed in MRI, the dose is preferably 0.1–10 g per person. When the agent is employed in PET, at least 0.01% of the agent is preferably replaced by the derivative comprising a radioisotope of fluorine. In PET, 1 ng–1 μg of the agent can be detected, and thus the dose of the agent may be reduced more.

EXAMPLES

The present invention will next be described in more detail by way of examples.

Reference Example 1

Synthesis of 1-[1-acetoxymethyl-2-(hydroxy) ethoxy]methyl-2-nitroimidazole

2-Nitroimidazole was subjected to trimethylsilylation by use of hexamethyldisilazane in acetonitrile, and the resultant compound and 2-acetoxymethoxy-1,3-diacetoxypropane were subjected to condensation by use of stannic chloride serving as a catalyst. The resultant product was deprotected by use of methanolic ammonia, to thereby obtain 1-[2-hydroxy-1-(hydroxymethyl)ethoxy]methyl-2-nitroimidazole. The thus-obtained 1-[2-hydroxy-1-(hydroxymethyl)ethoxy]methyl-2-nitroimidazole (0.5 g) was refluxed for two hours together with dibutyl tin oxide (0.6 g) in anhydrous toluene in the presence of molecular sieves having a pore size of 4 Å. The solvent was removed under reduced pressure, and anhydrous methylene chloride (16 mL) and anhydrous tetrahydrofuran (4 mL) were added to the residue. The resultant mixture was cooled to 0° C., and acetyl chloride (171 mg) was added to the mixture, and then the mixture was stirred for 30 minutes. To the resultant reaction mixture, a sodium phosphate buffer having a pH of 7.1 (10 mL) was added, and the resultant mixture was subjected to filtration. The resultant residue was subjected to extraction with chloroform (10 mL×3), and the thus-obtained extract was mixed with the filtrate, and the mixture was separated, thereby obtaining an organic layer. The organic layer was dried over sodium sulfate, and then fractionated and purified through silica gel chromatography, to thereby yield the title compound, 1-[1-acetoxymethyl-2-(hydroxy)ethoxy]methyl-2-nitroimidazole (265 mg).

Example 1

Synthesis of 1-[2-(toluene-4-sulfoxy)-1-(acetoxymethyl)ethoxy]methyl-2-nitroimidazole (compound 1)

1[-Acetoxymethyl-2-(hydroxy)ethoxy]methyl-2-nitroimidazole (117 mg) was placed in a flask together with anhydrous pyridine, toluenesulfonyl chloride (252 mg) was added to the flask, and the resultant mixture was stirred at room temperature for five hours. The reaction mixture was subjected to extraction with ethyl acetate (30 mL), and the resultant extract was partitioned and washed with water (30 mL×2). The resultant organic layer was dried over sodium sulfate, concentrated under reduced pressure, and purified through silica gel column chromatography, to thereby yield the title compound 1 (90.2 mg).

$^1$H-NMR (CD$_3$CN): δ ppm: 1.88 (s, 3H), 2.44 (s. 3H). 3.96~4.11 (m, 4H), 5.68, 5.78 (AB pattern ; J=1.0 Hz, 2H) 7.11 (d, J=8.5 Hz. 1H), 7.39 (d, J=1.0 Hz, 1H), 7.42 (d, J=8.5 Hz, 1H), 7.73 (d. J=8.5 Hz, 1H) $^{18}$C-NMR (CD$_3$CN): δ ppm 20.7, 21.6, 63.1, 69.8, 75.6, 78.5, 127.2, 128.8, 131.1, 171.1 Mass spectrum: 413 (M$^+$)

Example 2

Synthesis of 1-[1-1-acetoxymethyl-2-fluoroethoxy] methyl)-2-nitroimidazole (compound 2)

Acetonitrile (10 mL) was mixed with water (1 mL), and potassium fluoride (33.8 mg) and 18-crown-6 (80 mg) were added to the solution. The solution was dried under reduced pressure, compound 1 (89.2 mg) in anhydrous dimethylformamide (10 mL) was added to the above-dried solution, and the resultant mixture was heated at 110° C. for eight hours. After ethyl acetate (20 mL) was added to the resultant reaction mixture, the mixture was washed with water (20 mL). The water layer was subjected to extraction with ethyl acetate (20 mL×2), the resultant extract was mixed with the organic layer, and the resultant mixture was dried under reduced pressure. The dried product was purified through separable high performance chromatography, to thereby yield the title compound 2 (16.2 mg).

$^1$H-NMR (CD$_3$CN): δ ppm 1.94 (s. 3H), 3.98~4.14 (m, 3H). 4.38~4.58 (m, 2H) 5.79, 5.86 (AB, pattern; J=1.2 Hz, 2H), 7.13 (d, J=1.2 Hz, 1H), 7.51 (d, J=1.1 Hz, 1H) $^{13}$C-NMR (CD$_3$CN): δ ppm 20.8, 62.9, 76.7, 78.8, 83.6, 127.2, 128.8, 171.3 Mass spectrum: 261 (M$^+$)

Example 3

Synthesis of 1-[2-fluoro-1-(hydroxymethyl)ethoxy]methyl-2-nitroimidazole (compound 3)

A 50 V/V% aqueous solution of ethanol (2 mL) containing sodium hydroxide (0.05 N) was added to compound 2 of Example 2 (18 mg), and the mixture was stirred at 40' C. for 1.5 minutes. The resultant reaction mixture was added to an ion exchange column to remove sodium cation. Thereafter, the resultant mixture was concentrated under reduced pressure, and then purified through separable high performance chromatography, to thereby yield the title compound 3 (10.3 mg).

$^1$H-NMR (CD$_3$CN): δ ppm 3.01 (b r, 1H), 3.49~3.53 (m, 2H), 4.32~4.54 (m, 2H), 5.83, 5.85 (AB pattern; J=10.8 Hz, 2H), 7.11 (d, J=1.1 Hz, 1H), 7.51 (d, J=1.1 Hz, 1H)

$^{13}$C-NMR (CD$_3$CN): δ ppm 61.1, 79.1, 79.9, 84.1, 127.0, 128.8 Mass spectrum 220.07 (M$^+$)

Example 4

Synthesis of 1-[2-fluoro($^{18}$F)-1-(hydroxymethyl)ethoxy]methyl-2-nitroimidazole (compound 4)

In a manner similar to those as described in Examples 1 and 2, 1-[2-(toluene-4-sulfoxy)-1-(acetoxymethyl)ethoxy]methyl-2-nitroimidazole was reacted with K$^{18}$F (prepared by use of a cyclotron HW-12, 3.7 GBq) by use of cryptofix 2.2.2 serving as a phase transfer catalyst, to thereby yield the title compound 4 (150 MBq). Through high performance liquid chromatography, compound 4 was found to have elution properties which are the same as those of 1-[2-fluoro-1-(hydroxymethyl)ethoxy]methyl-2-nitroimidazole (compound 3) of Example 3. Therefore, compound 4 was found to be a compound in which a fluorine atom of compound 3 was replaced by $^{18}$F.

Test Example 1

Imaging of an ischemic site of the heart was carried out by use of compound 4 of Example 4.

A male Donryu rat was anesthetized with pentobarbital, and the respiration of the rat was regulated by use of a respirator. The left chest of the rat was opened at the position between the seventh and eighth sterna, and the pericardium was incised for exposure of the heart. The left anterior descending artery stem of the coronary artery was ligated in order to induce ischemia. Separately, compound 4 was diluted with compound 3 so as to attain a radiation intensity of 150 MBq. The thus-diluted compound 4 was administered intravenously to the rat 15 minutes after completion of ligation. The heart was extirpated 40 minutes after administration of the compound 4, a frozen section of the heart was prepared, and the section was brought into contact with an imaging plate, to thereby obtain an autoradiogram thereof as shown in FIG. 1.

The autoradiogram revealed that the diagnostic imaging agent of the present invention exists at relatively high Id concentration at a muscle tissue site in the vicinity of the left ventricle, at which ischemia is usually generated by such ligation, and thus the agent appropriately images an ischemic site.

Test Example 2

Compound 4 of Example 4 was intravenously injected to cancer-bearing mice (WHT/Ht albino mice) (3 mice per group). Systemic frozen sections of each mouse were prepared 10, 30, 60, 120, and 150 minutes after intravenous injection, and the radiation intensity of each organ was measured. Squamous-cell carcinoma and fibrosarcoma were employed as cancer sources. When the sections was prepared, blood was collected separately, and the ratio of radiation intensity in each organ to that in blood was obtained. The results are shown in Table 1.

TABLE 1

| Organ | 10 min. | 30 min. | 60 min. | 120 min. | 150 min. |
|---|---|---|---|---|---|
| Brain | 1.168 | 0.815 | 0.308 | 0.116 | 0.126 |
| Lung | 2.151 | 1.347 | 0.596 | 0.353 | 0.331 |
| Heart | 1.721 | 0.929 | 0.378 | 0.216 | 0.186 |
| Liver | 10.300 | 5.018 | 1.692 | 0.730 | 0.800 |
| Kidney | 7.935 | 5.667 | 1.856 | 0.699 | 0.511 |
| Muscle | 1.576 | 0.742 | 0.314 | 0.139 | 0.159 |
| Bone | 1.157 | 0.617 | 0.244 | 0.253 | 0.218 |
| Testis | 0.861 | 0.852 | 0.466 | 0.412 | 0.139 |
| Intestine | 1.697 | 0.767 | 0.533 | 0.56 | 0.488 |
| Blood | 2.222 | 1.068 | 0.379 | 0.117 | 0.096 |
| Fibrosarcoma | 1.584 | 1.319 | 0.619 | 0.421 | 0.351 |
| Fibrosarcoma/blood | 0.697 | 1.234 | 1.634 | 3.601 | 3.675 |
| Squamous carcinoma | 2.192 | 1.237 | 0.466 | 0.133 | 0.101 |
| Squamous carcinoma/blood | 0.893 | 1.012 | 1.384 | 2.904 | 2.357 |

Table 1 shows that the concentrations of compound (1) in the tumor are higher than in the blood or the other organs except those which are related with metabolism of this compound. Especially the ratio of the concentration in the tumor to that in the blood is in the range of 2–4. In addition, the concentrations of this compound in fibrosarcoma are higher than in squamous carcinoma, which has less hypoxic cells. Those teach us that the compound (1) of the present invention selectively distributes to the tumor, especially to the hypoxic sites of the tumor, and can be recognized due to the presence of a radioisotope.

Figure 2:
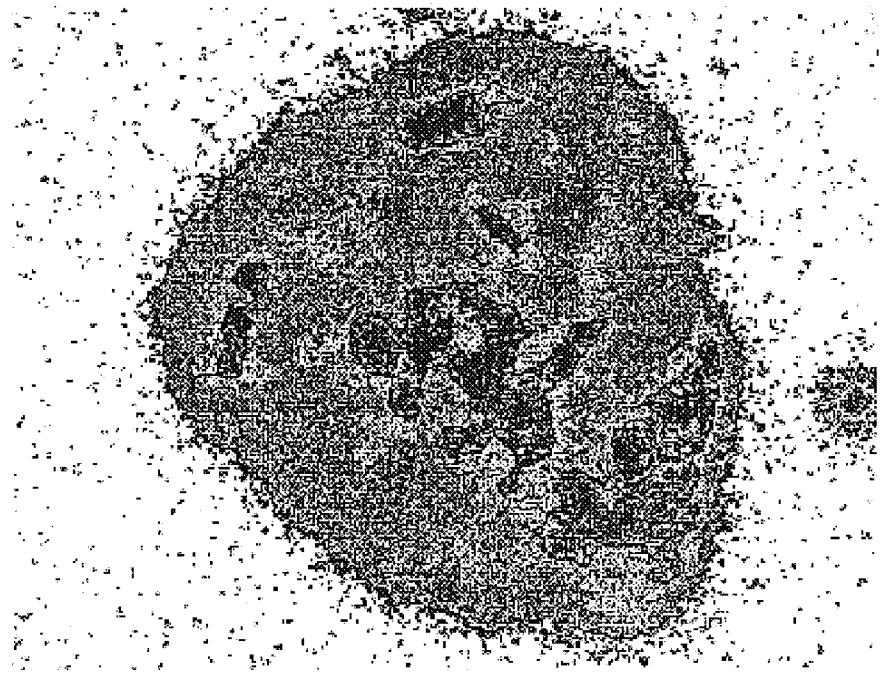
FIG. 2 is an autoradiogram of a tumor, which is obtained by use of the diagnostic imaging agent of the present invention.

In addition, an autoradiogram of a portion in the vicinity of the tumor was obtained 120 minutes after intravenous injection of the compound (1). The autoradiogram is shown in FIG. 2. The autoradiogram revealed that the compound (1) of the present invention is roughly spread over the entirety of the tumor relatively deeply. Also, it was found that the compound is located in the vicinity of necrotic portion of the tumor, and that the position at which the compound is located is identical with the position of chemotherapeutic-agent-resistant or radiation-resistant cancer cells. Therefore, the compound (1) of the present invention was found to be useful as a diagnostic imaging agent of cancer cells.

Industrial Applicability

The nitroimidazole derivative (1) of the present invention enables imaging of the ischemic sites of circulatory organs, which are caused by circulatory organ diseases, or imaging of cancer cells such as agent-resistant or radiation-resistant hypoxic cancer cells, and thus the derivative can provide information about the position and the amount of ischemic sites or such cancer cells. Therefore, the derivative greatly contributes to selection of appropriate treatment of ischemia or cancer.

What is claimed is:

1. A nitroimidazole derivative represented by the following formula (1):

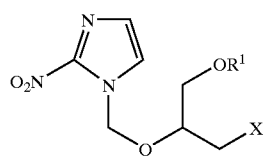

wherein $R^1$ represents a hydrogen atom or a $C_1$–$C_4$ alkanoyl group; and X represents a fluorine atom or an isotope thereof.

2. The nitroimidazole derivative according to claim 1, wherein X is $^{18}$F.

3. A diagnostic imaging agent comprising, as an active ingredient, a nitroimidazole derivative as recited in claim 1.

4. A diagnostic imaging agent comprising, as an active ingredient, a nitroimidazole derivative as recited in claim 2.

5. A method of diagnostic imaging comprising administration of a nitroimidazole derivative as recited in claim 1 for imaging.

6. A method of diagnostic imaging comprising administration of a nitroimidazole derivative as recited in claim 2 for imaging.

7. The method of diagnostic imaging according to claim 5, wherein an ischemic site or cancer cell is imaged.

8. The method of diagnostic imaging according to claim 6, wherein an ischemic site or cancer cell is imaged.

9. The method according to claim 7, wherein a cancer cell is imaged and wherein the cancer cell is a chemotherapeutic-agent-resistant or radiation-resistant cancer cell.

10. The method according to claim 8, wherein a cancer cell is imaged and wherein the cancer cell is a chemotherapeutic-agent-resistant or radiation-resistant cancer cell.

11. A nitroimidazole derivative represented by the following formula (2):

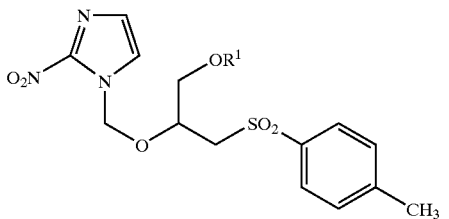

wherein $R^1$ represents a hydrogen atom or a $C_1$–$C_4$ alkanoyl group.

12. A method for producing a nitroimidazole derivative as recited in claim 1, comprising fluorination of a nitroimidazole derivative represented by the following formula (2):

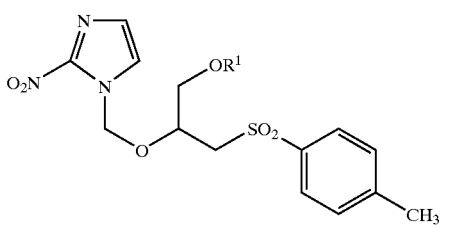

wherein $R^1$ represents a hydrogen atom or a $C_1$–$C_4$ alkanoyl group.

13. The nitroimidazole derivative according to claim 1, wherein $R^1$ represents a hydrogen atom.

14. The nitroimidazole derivative according to claim 1, wherein $R^1$ represents an acetyl group.

15. The nitroimidazole derivative according to claim 2, wherein $R^1$ represents a hydrogen atom.

16. The nitroimidazole derivative according to claim 2, wherein $R^1$ represents an acetyl group.

17. The nitroimidazole derivative according to claim 1, which is 1-[2-fluoro($^{18}$F or $^{19}$F)hydroxymethyl)ethoxy]methyl-2-nitroimidazole or 1-[1-acetoxymethyl-2-fluoro($^{18}$F or $^{19}$F)ethoxy]methyl-2-nitroimidazole.

* * * * *

UNITED STATES PATENT AND TRADEMARK OFFICE
CERTIFICATE OF CORRECTION

PATENT NO. : 6,743,925 B1
DATED : June 1, 2004
INVENTOR(S) : Yoshihiro Takai et al.

It is certified that error appears in the above-identified patent and that said Letters Patent is hereby corrected as shown below:

<u>Column 10,</u>
Line 40, "which is 1-[2-fluoro($^{18}$F or $^{19}$F)hydroxymethyl]ethoxy]methyl-2-nitroimidazole" should read -- 1-[2-fluoro($^{18}$F or $^{19}$F)-1-hydroxymethyl]ethoxy]methyl-2-nitroimidazole --.

Signed and Sealed this

Fifteenth Day of March, 2005

JON W. DUDAS
*Director of the United States Patent and Trademark Office*